US008597179B2

(12) United States Patent
Kokubo

(10) Patent No.: US 8,597,179 B2
(45) Date of Patent: Dec. 3, 2013

(54) ENDOSCOPE APPARATUS

(75) Inventor: Mitsutaka Kokubo, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 56 days.

(21) Appl. No.: 12/907,297

(22) Filed: Oct. 19, 2010

(65) Prior Publication Data

US 2011/0092769 A1    Apr. 21, 2011

Related U.S. Application Data

(63) Continuation of application No. PCT/JP2010/058511, filed on May 20, 2010.

(30) Foreign Application Priority Data

Jul. 23, 2009 (JP) .................................. 2009-172420

(51) Int. Cl.
*A61B 1/04* (2006.01)

(52) U.S. Cl.
USPC ........... 600/169; 600/109; 600/112; 600/160; 600/161; 600/174; 600/175; 600/176

(58) Field of Classification Search
USPC .......... 600/109, 112, 160, 161, 169, 174–176
See application file for complete search history.

(56) References Cited

U.S. PATENT DOCUMENTS

| 4,646,723 | A | 3/1987 | Arakawa | |
|---|---|---|---|---|
| 8,182,421 | B2 * | 5/2012 | Muckner et al. | ............... 600/169 |
| 2006/0058584 | A1 * | 3/2006 | Hirata | ............................ 600/179 |
| 2006/0069312 | A1 * | 3/2006 | O'Connor | ...................... 600/176 |
| 2006/0161047 | A1 * | 7/2006 | Miyoshi | ......................... 600/157 |
| 2009/0253966 | A1 | 10/2009 | Ichimura | |
| 2010/0201794 | A1 * | 8/2010 | Kido et al. | ....................... 348/65 |

FOREIGN PATENT DOCUMENTS

| EP | 1 880 656 A1 | 1/2008 |
|---|---|---|
| JP | 59-127934 | 3/1986 |
| JP | 03-118021 | 5/1991 |

(Continued)

OTHER PUBLICATIONS

International Search Report dated Aug. 10, 2010.

(Continued)

*Primary Examiner* — Matthew J Kasztejna
*Assistant Examiner* — Kevin G Barry, III
(74) *Attorney, Agent, or Firm* — Scully, Scott, Murphy & Presser, P.C.

(57) ABSTRACT

An endoscope apparatus includes an insertion portion inserted into a body, an optical member arranged exposed from an outside surface at a distal end of the insertion portion, an objective optical system that condenses light impinged from the optical member, an electronic image pickup circuit that photoelectrically converts the light condensed by the objective optical system, a heat absorbing section arranged in the vicinity of the electronic image pickup circuit for absorbing heat generated from the electronic image pickup circuit, a heat transfer section extending toward the optical member side for transferring heat of the heat absorbing section, a heat radiation section arranged in the vicinity of the optical member for radiating heat transferred by the heat transfer section to the optical member, and a heat transfer member that is formed by patterning a metal foil on an insulating, flexible film member and includes the heat absorbing section, the heat transfer section and the heat radiation section.

8 Claims, 8 Drawing Sheets

(56) References Cited

FOREIGN PATENT DOCUMENTS

| | | |
|---|---|---|
| JP | 08-009208 | 1/1996 |
| JP | 11-032985 | 2/1999 |
| JP | 2003-284686 | 10/2003 |
| JP | 2003-334157 | 11/2003 |
| JP | 2004-020798 | 1/2004 |
| JP | 2006-314459 | 11/2006 |
| JP | 2008-259611 | 10/2008 |
| JP | 2009-066223 | 4/2009 |
| JP | 2009-082503 | 4/2009 |
| JP | 2010-069217 | 4/2010 |
| WO | WO 2006/120797 A1 | 11/2006 |
| WO | WO 2009/041724 A1 | 4/2009 |

OTHER PUBLICATIONS

Japanese Office Action dated Feb. 22, 2011 together with an English language translation.

Extended Supplementary European Search Report dated May 23, 2012 issued in counterpart European Patent Application No. 10802120.5.

* cited by examiner

ENDOSCOPE APPARATUS

CROSS REFERENCE TO RELATED APPLICATION

This application is a continuation application of PCT/JP2010/058511 filed on May 20, 2010 and claims benefit of Japanese Application No. 2009-172420 filed in Japan on Jul. 23, 2009, the entire contents of which are incorporated herein by this reference.

BACKGROUND OF THE INVENTION

1. Field of the Invention

The present invention relates to an endoscope apparatus equipped with an image pickup apparatus, and more particularly, to an endoscope apparatus capable of preventing fogging, condensation or the like on the surface of an objective optical system provided to observe a subject.

2. Description of the Related Art

As is well known, endoscope apparatuses are widely used for observation, treatment or the like of the inside of the body (inside the body cavity) of a living body or inspection, repair or the like inside industrial plant equipment. In recent years, electronic endoscope apparatuses equipped with an image pickup apparatus such as a CCD are the mainstream among endoscope apparatuses.

Furthermore, an endoscope apparatus may be subject to fogging in its objective optical system caused by condensation produced due to a temperature difference between an outside air temperature and ambient temperature of a subject to be examined or ambient humidity of the subject to be examined or the like. Therefore, various kinds of technique are proposed to prevent fogging, condensation or the like from occurring in objective optical systems of endoscope apparatuses.

For example, an image pickup apparatus of an endoscope disclosed in Japanese Patent Application Laid-Open Publication No. 2003-284686 is configured such that an air gap is provided between a CCD and a cover glass, a peripheral circuit is disposed above the outer surface located on the prism side of the cover glass so that heat generated from this peripheral circuit is constantly transmitted to the cover glass. Thus, according to Japanese Patent Application Laid-Open Publication No. 2003-284686, when the observation optical system is drastically cooled with cleaning water jetted over an observation window, the cover glass cooled via a lens barrel and the prism receives heat from the peripheral circuit, which reduces the temperature difference between the outer surface located on the prism side and the inner surface located on the air gap side, preventing fogging on the inner surface caused by moisture in the air gap.

Furthermore, for example, in an anti-fogging apparatus of a rigid endoscope disclosed in Japanese Patent Application Laid-Open Publication No. 2003-334157, a heating light guide is inserted into an insertion portion of the rigid endoscope and a dual function light-shielding/heat transfer metal plate that shields light guided by the heating light guide and converts the shielded light to heat warms a light receiving lens and thereby prevents fogging from occurring on the light-receiving lens.

SUMMARY OF THE INVENTION

A first endoscope apparatus of the present invention is provided with an insertion portion inserted into a body, an optical member arranged exposed from an outside surface at a distal end of the insertion portion, an objective optical system that condenses light impinged from the optical member, an electronic image pickup circuit that photoelectrically converts the light condensed by the objective optical system, a heat absorbing section arranged in the vicinity of the electronic image pickup circuit for absorbing heat generated from the electronic image pickup circuit, a heat transfer section extending toward the optical member side for transferring heat of the heat absorbing section, a heat radiation section arranged in the vicinity of the optical member for radiating heat transferred by the heat transfer section to the optical member, and a heat transfer member that is formed by patterning a metal foil on an insulating, flexible film member and includes the heat absorbing section, the heat transfer section and the heat radiation section.

Furthermore, a second endoscope apparatus of the present invention is provided with an insertion portion inserted into a body, an optical member arranged exposed from an outside surface at a distal end of the insertion portion, an objective optical system that condenses light impinged from the optical member, an electronic image pickup circuit that photoelectrically converts the light condensed by the objective optical system, heat absorbing means arranged in the vicinity of the electronic image pickup circuit for absorbing heat generated from the electronic image pickup circuit, heat transferring means extending toward the optical member side for transferring heat of the heat absorbing means, heat radiating means arranged in the vicinity of the optical member for radiating heat transferred by the heat transferring means to the optical member, and heat transfer means that is formed by patterning a metal foil on an insulating, flexible film member and includes the heat absorbing means, the heat transferring means and the heat radiating means.

DETAILED DESCRIPTION OF THE PREFERRED EMBODIMENTS

Hereinafter, embodiments of the present invention will be described with reference to the accompanying drawings.

(First Embodiment)

First, a first embodiment of the present invention will be described.

Figure 1:
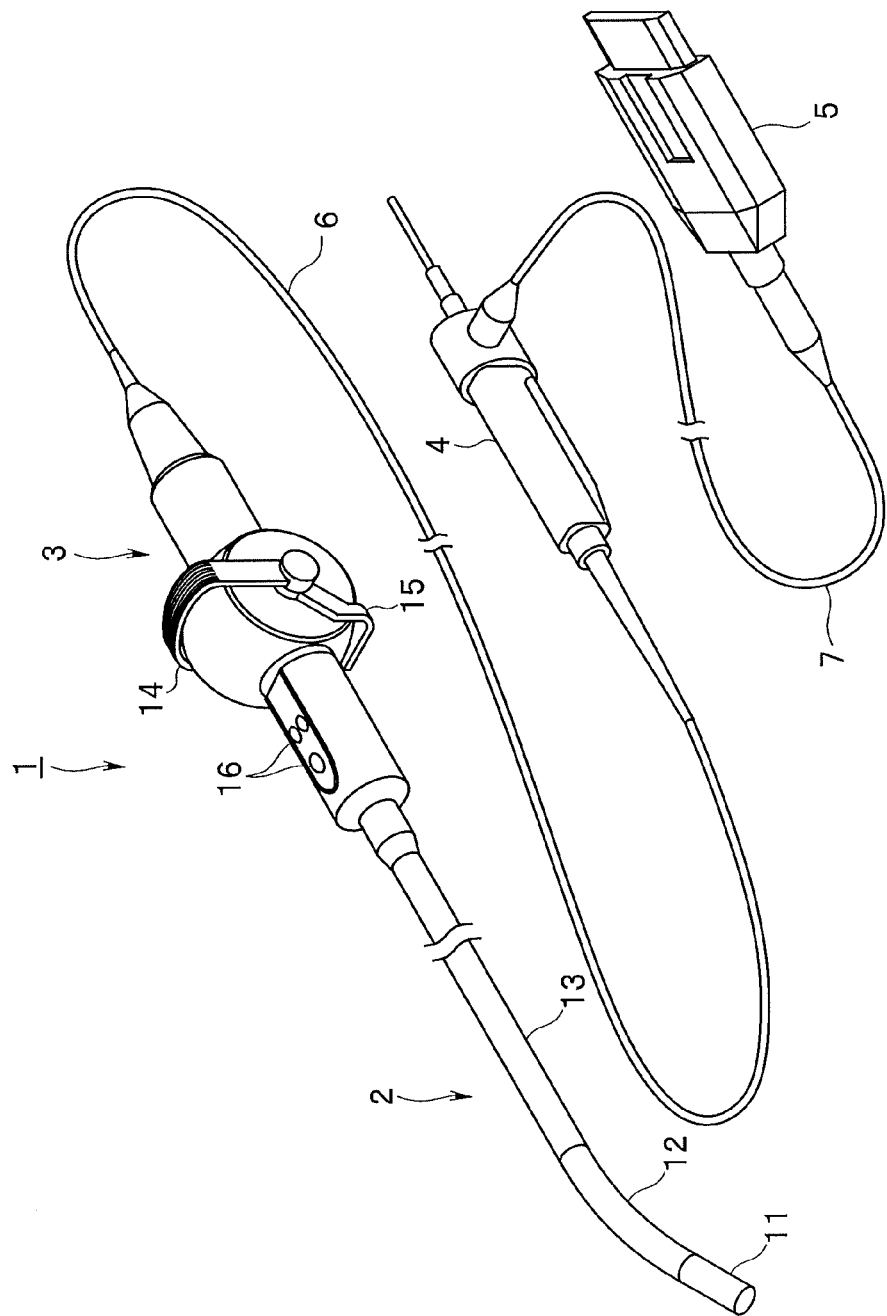
FIG. 1 is a perspective view illustrating an overall configuration of an endoscope apparatus according to a first embodiment of the present invention.
Figure 2:
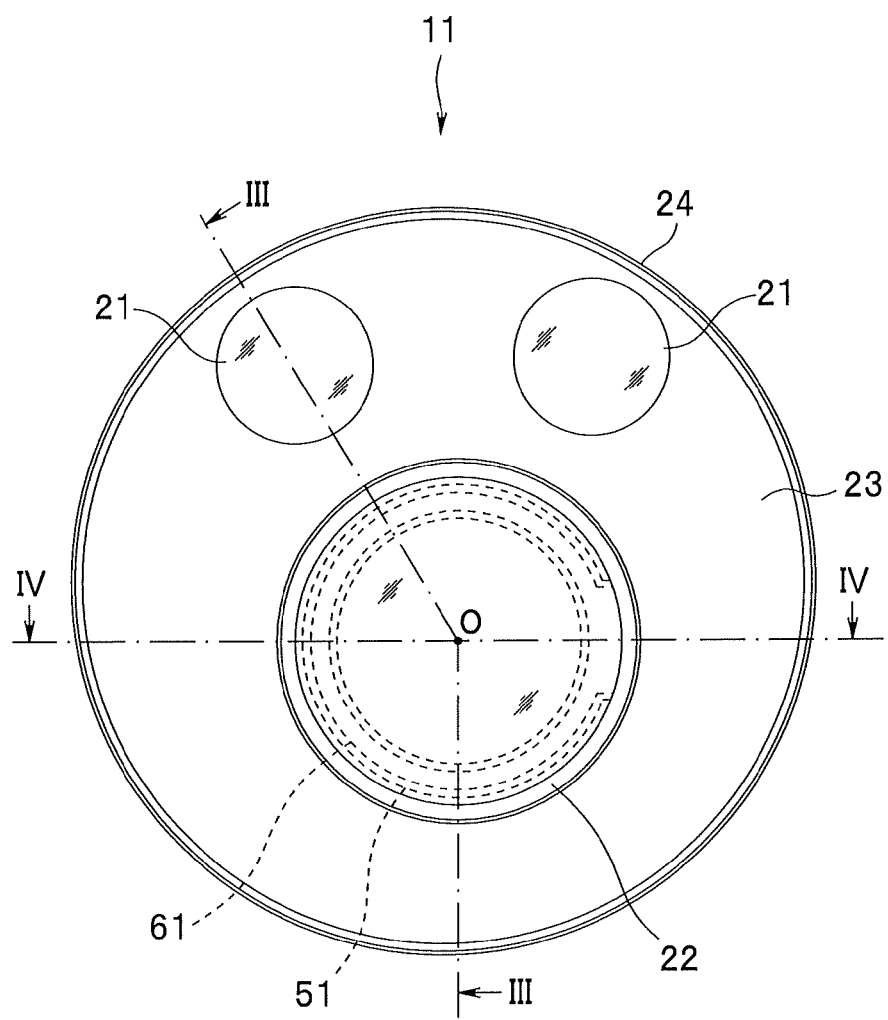
FIG. 2 is a front view of a distal end portion of an insertion portion according to the first embodiment of the present invention.
Figure 3:
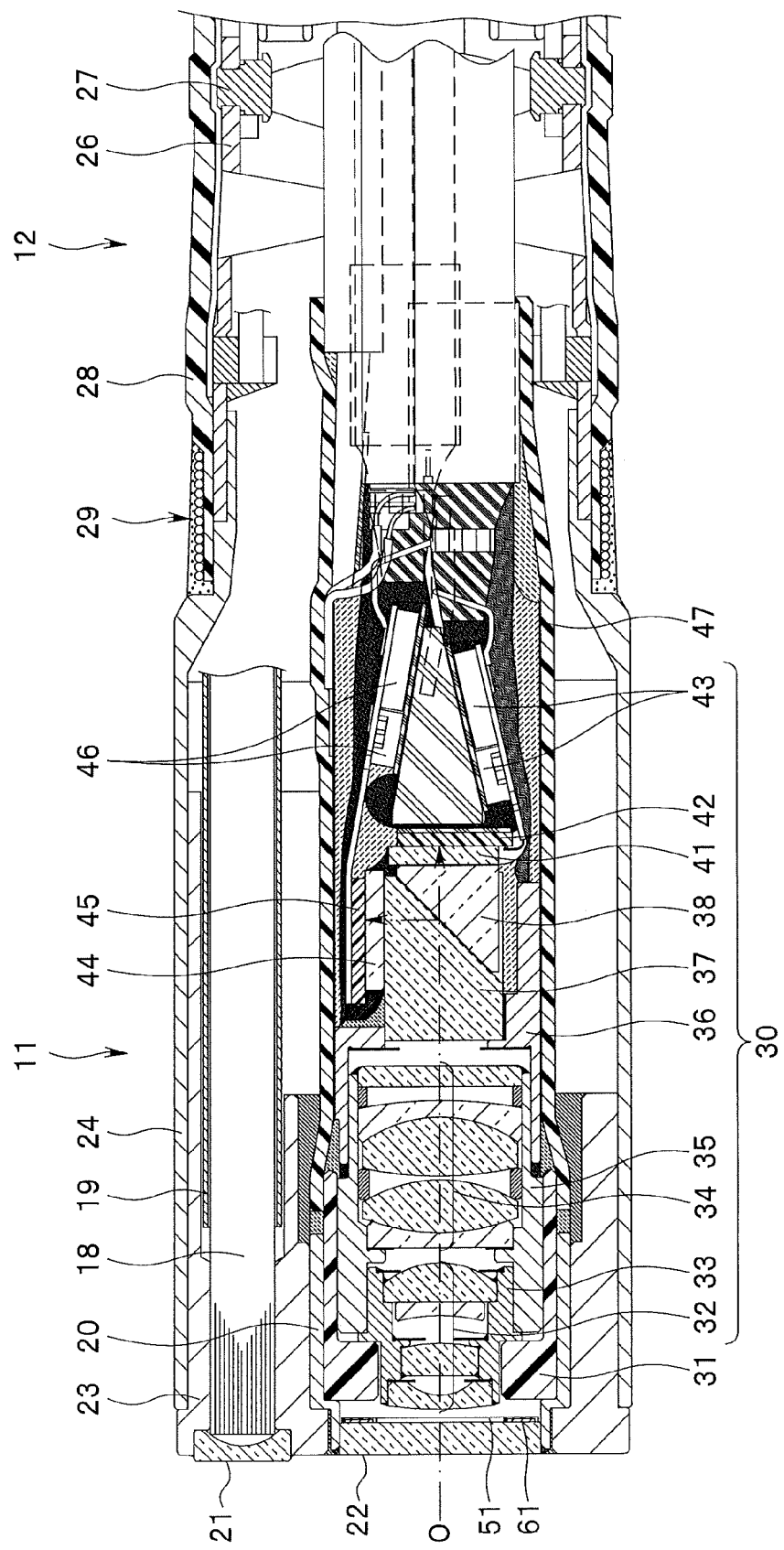
FIG. 3 is a cross-sectional view of the distal end portion of the insertion portion along a line of FIG. 2 according to the first embodiment of the present invention.
Figure 4:
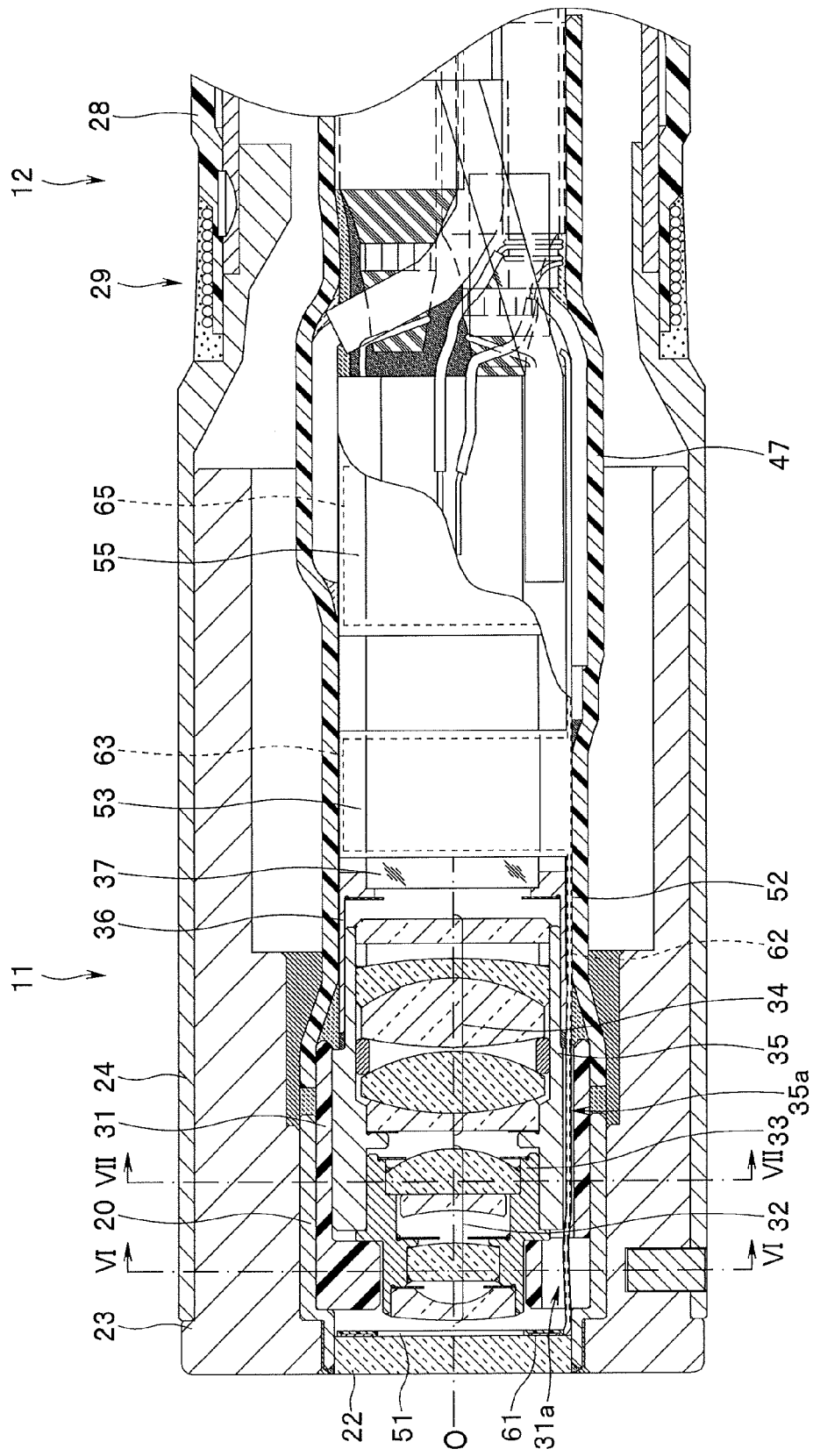
FIG. 4 is a cross-sectional view of the distal end portion of the insertion portion along a line IV-IV of FIG. 2 according to the first embodiment of the present invention.
Figure 5:
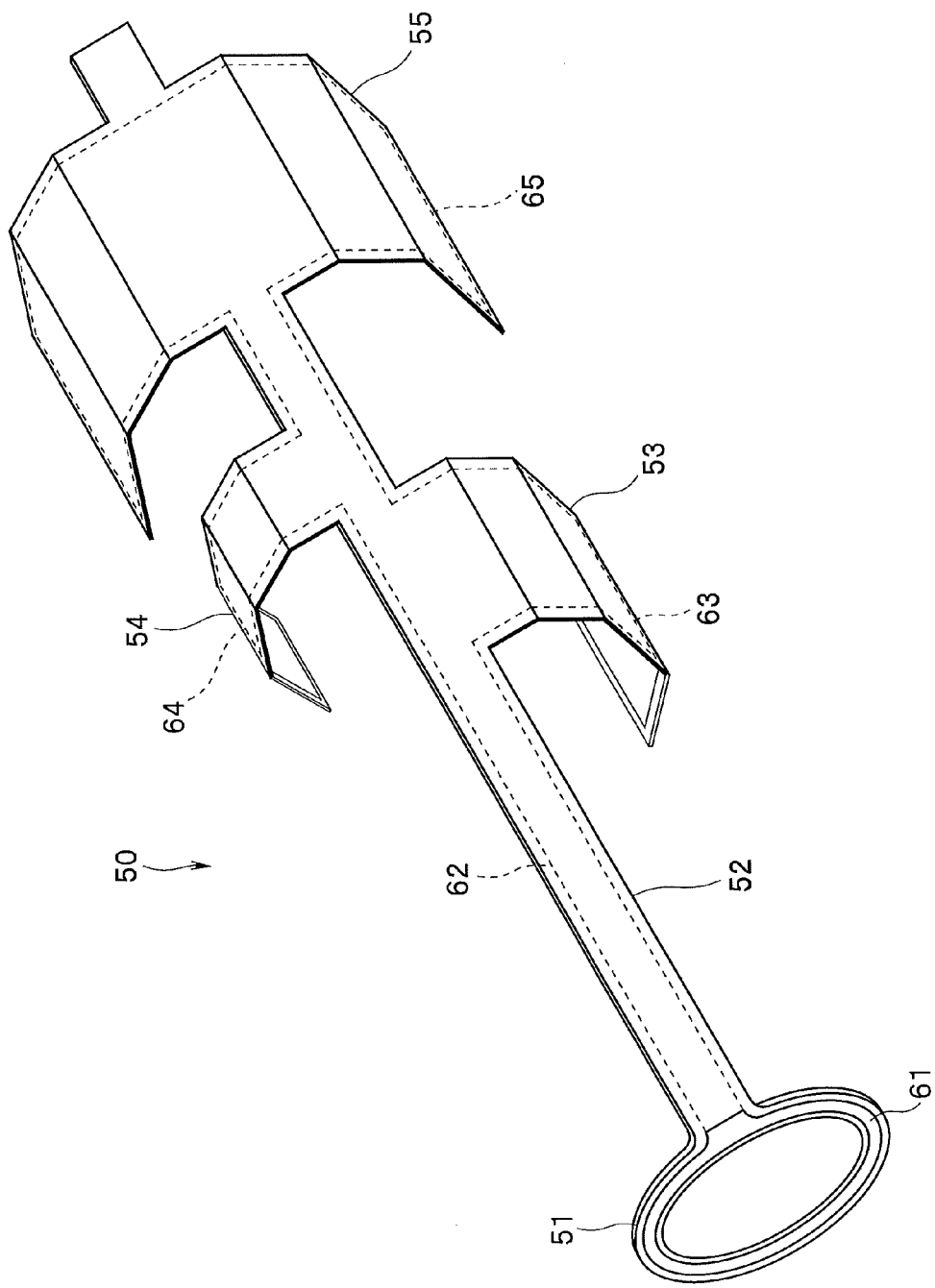
FIG. 5 is a perspective view illustrating a configuration of a heat transfer member according to the first embodiment of the present invention.
Figure 6:
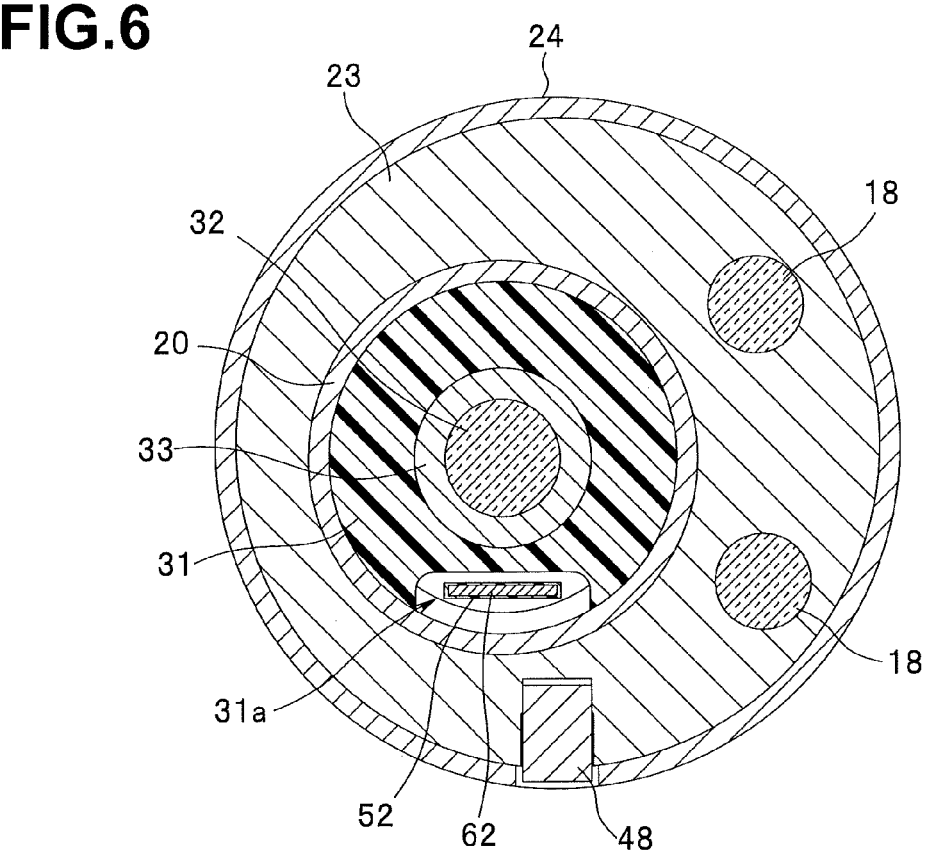
FIG. 6 is a cross-sectional view of the distal end portion of the insertion portion along a line VI-VI of FIG. 4 according to the first embodiment of the present invention.
Figure 7:
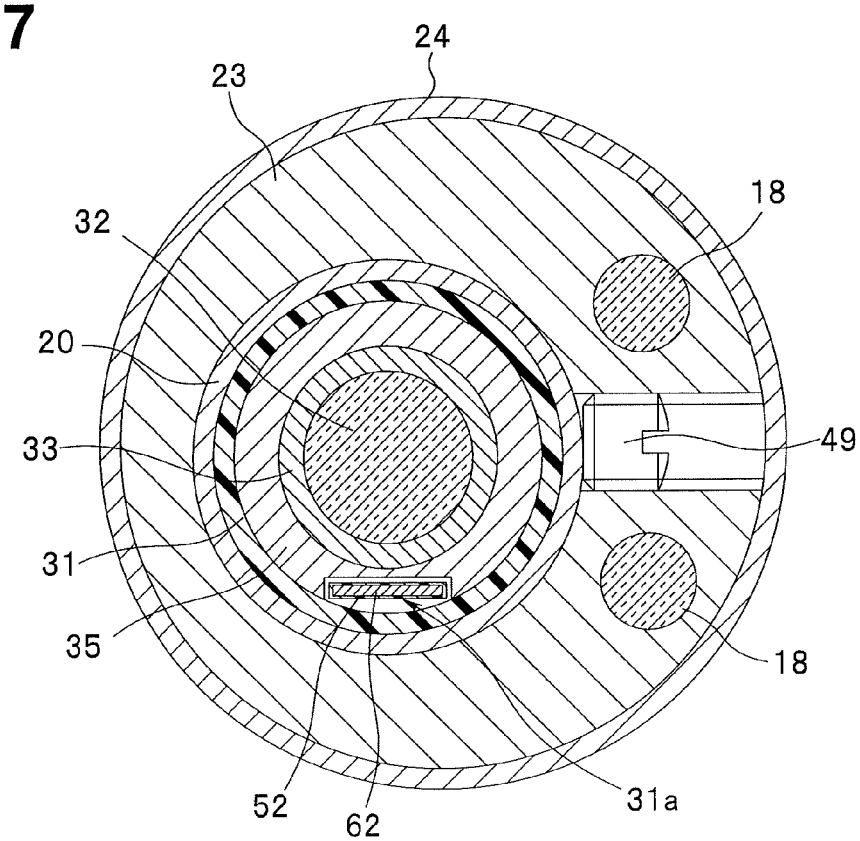
FIG. 7 is a cross-sectional view of the distal end portion of the insertion portion along a line VII-VII of FIG. 4 according to the first embodiment of the present invention.
Figure 8:
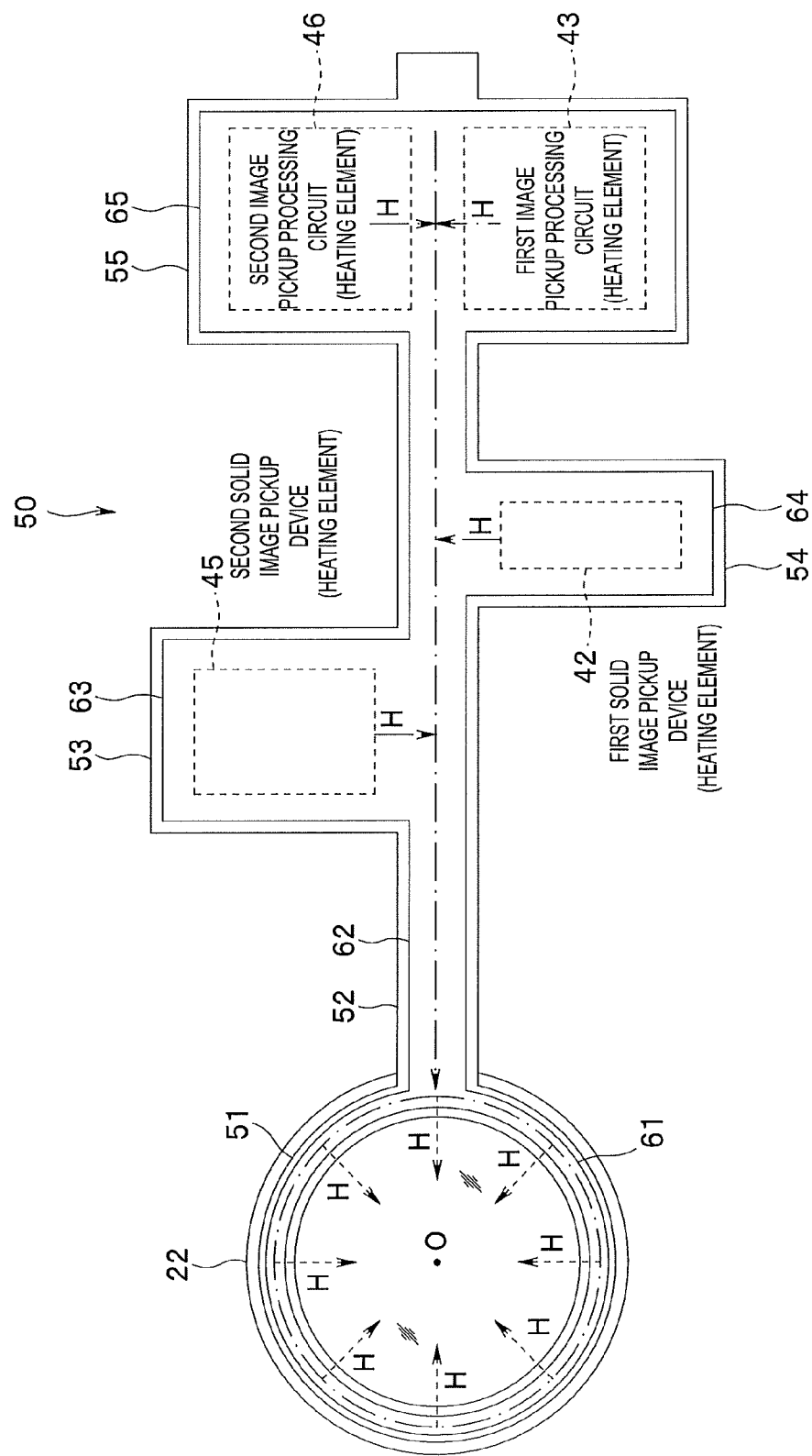
FIG. 8 is a diagram illustrating heat transfer operation by the heat transfer member according to the first embodiment of the present invention.

FIG. 1 to FIG. 8 are related to the first embodiment of the present invention, FIG. 1 is a perspective view illustrating an overall configuration of an endoscope apparatus, FIG. 2 is a front view of a distal end portion of an insertion portion, FIG. 3 is a cross-sectional view of the distal end portion of the insertion portion along a line III-III of FIG. 2, FIG. 4 is a cross-sectional view of the distal end portion of the insertion portion along a line IV-IV of FIG. 2, FIG. 5 is a perspective view illustrating a configuration of a heat transfer member, FIG. 6 is a cross-sectional view of the distal end portion of the insertion portion along a line VI-VI of FIG. 4, FIG. 7 is a cross-sectional view of the distal end portion of the insertion portion along a line VII-VII of FIG. 4 and FIG. 8 is a diagram illustrating heat transfer operation by the heat transfer member.

As shown in FIG. 1, an endoscope apparatus 1 is configured by mainly including an elongated insertion portion 2, an operation section 3 connected to a proximal end of the insertion portion 2, a light guide connector 4 connected to a light source device (not shown) and a video connector 5 connected to a video system center (not shown). In the endoscope apparatus 1, the operation section 3 and the light guide connector 4 are connected via a flexible cable 6 and the light guide connector 4 and the video connector 5 are connected via a communication cable 7.

The insertion portion 2 is connected to a distal end portion 11 mainly made of a metallic member such as stainless steel, a bending portion 12 and a rigid tube 13 which is a metal tube such as stainless steel, connected in that order from the distal end side. The insertion portion 2 is a portion inserted into the body and incorporates a cable and a light guide or the like as will be described later.

The operation section 3 is provided with angle levers 14 and 15 for remotely operating the bending portion 12, and various switches 16 for operating the light source device, the video system center or the like. The angle levers 14 and 15 are bending operation means capable of operating the bending portion 12 of the insertion portion 2 in four directions, up, down, left and right. The endoscope apparatus 1 of the present embodiment is a rigid endoscope apparatus, in which much of the insertion portion 2 other than the bending portion 12 is rigid.

Next, an internal configuration of the distal end of the insertion portion 2 of the endoscope apparatus 1 will be described in detail based on FIG. 2 to FIG. 4.

As shown in FIG. 2, an illumination lens 21 which serves as an illumination window for illumination and a transparent cover member 22 which is an optical member serving as an observation window for image pickup are arranged so as to be exposed from the front (front end face) of the distal end portion 11 of the endoscope apparatus 1. The endoscope apparatus 1 of the present embodiment is equipped with two illumination lenses 21 on the front of the distal end portion 11.

As shown in FIG. 3 and FIG. 4, the distal end portion 11 of the insertion portion 2 has a metallic distal end rigid portion 23. The distal end rigid portion 23 engages with and holds the two illumination lenses 21 and penetrates and holds an image pickup unit 30 together with the transparent cover member 22. Furthermore, the distal end rigid portion 23 also engages with and holds a distal end portion of a light guide bundle 18 that transmits illuminating light behind each illumination lens 21.

The distal end rigid portion 23 is fitted in a metallic outer tube 24 and fixed to the outer tube 24 by a fixing pin 48 (see FIG. 6). At the proximal end of the outer tube 24, the distal end rigid portion 23 is coupled with a bending piece 26 arranged in the bending portion 12. A plurality of such bending pieces 26 are arranged in the bending portion 12. The neighboring bending pieces 26 are pivotably coupled via a pivotal rivet 27.

The bending portion 12 has a flexible tube 28 made of fluorine rubber or the like so as to integrally cover the outer circumference of the plurality of bending pieces 26. The distal end outer circumferential portion of the flexible tube 28 is connected to the proximal end of the outer tube 24 by means of a bobbin bonding section 29.

In the two light guide bundles 18 whose distal end portions are held by the distal end rigid portion 23, the distal end side is branched and the branched portions are bundled into one from some midpoint to the proximal end. The light guide bundle 18 is inserted and arranged through the insertion portion 2, the operation section 3 of the endoscope apparatus 1 up to the light guide connector 4. The two optical transmission paths branched on the distal end side of the light guide bundle 18 are inserted into two tubular members 19.

These two tubular members 19 are also fitted into and held in the distal end rigid portion 23. The portions from some midpoint to the proximal end side of the light guide bundle 18 are bundled and passed through a flexible tube (not shown) connected to the two tubular members 19.

The transparent cover member 22 which is an optical member is engaged with and held in a metallic first support frame 20 formed into a quasi-ring shape. The first support frame 20 is fitted in and fixed to the distal end rigid portion 23. A second support frame 31 in which the image pickup unit 30 is fitted and fixed is engaged with the first support frame 20 behind the transparent cover member 22. Furthermore, the first support frame 20 fitted in the distal end rigid portion 23 is fixed by a fixing screw 49 (see FIG. 7).

The second support frame 31 is a non-metallic quasi-ring-shaped member made of ceramics or the like to secure electric insulating properties of the image pickup unit 30.

The image pickup unit 30 of the present embodiment has a known configuration and includes a first lens holding frame 33 that holds a first objective lens group 32 which is an objective optical system, a second lens holding frame 35 that holds a second objective lens group 34 which is an objective optical system and a unit holding frame 36 that holds an image sensor or the like.

The first lens holding frame 33 is fitted in and fixed to the second lens holding frame 35. The second lens holding frame 35 is fitted in and fixed to the unit holding frame 36.

The image sensor or the like held by the unit holding frame 36 of the present embodiment is configured to include two solid image pickup devices (hereinafter simply referred to as "image pickup devices") 42 and 45 such as CCD or CMOS making up part of an electronic image pickup circuit that detects photographing light (shown by an optical axis O in the figure) condensed by objective lens groups 32 and 34 and separated by two prisms 37 and 38.

The first image pickup device 42 is connected to one surface of the prism 38 located therebehind via a cover glass 41. On the other hand, the second image pickup device 45 is connected to one surface of the prism 37 located in front thereof via a cover glass 44.

The surfaces of the two prisms 37 and 38 of the present embodiment are pasted to each other and their reflecting surfaces are formed so as to reflect only a predetermined wavelength band of visible light. To be more specific, the two prisms 37 and 38 are set so that only G (Green) light is refracted on the reflecting surfaces, B (Blue) light and R (Red) light are guided to the first image pickup device 42 and G (Green) light is guided to the second image pickup device 45.

Furthermore, the image pickup devices 42 and 45 have a configuration whereby image processing is performed individually and are connected to two image pickup processing circuits 43 and 46 making up part of the electronic image pickup circuit. The image pickup processing circuits 43 and 46 are connected to a communication cable which extends to the video connector 5 by passing through the insertion portion 2, operation section 3 and light guide connector 4.

As shown above, the image pickup unit 30 of the present embodiment separates incident visible light into two wavelength bands through the two prisms 37 and 38. The image pickup unit 30 is provided with the two image pickup processing circuits 43 and 46 that photoelectrically convert the two light beams detected through the two image pickup devices 42 and 45 into signals and process the signals, and are thus configured to be able to acquire observed images of high resolution and high quality color reproduction.

Perimeters of the components held in the unit holding frame 36 together with a filling agent or the like are covered with a thermal contraction tube 47. This thermal contraction tube 47 integrally covers the portion from the proximal end outer circumferential portion of the second support frame 31 to the distal end outer circumferential portion of the communication cable.

In this way, the first support frame 20 that holds the transparent cover member 22 and whose distal end side is closed and the second support frame 31 are hermetically engaged with each other, and the portion from the proximal end outer circumferential portion of the second support frame 31 to the distal end outer circumferential portion of the communication cable is covered with the thermal contraction tube 47, and therefore the image pickup unit 30 is hermetically sealed inside the distal end portion 11.

Furthermore, the endoscope apparatus 1 of the present embodiment is provided with a heat transfer member 50 (see FIG. 5) which is heat conduction means that transmits heat generated in the distal end portion 11 by the image pickup unit 30 to the transparent cover member 22.

More specifically, as shown in FIG. 5, the heat transfer member 50 is a flexible thin film member provided with a heat radiation section 51 which is thin-film ring-shaped heat radiating means, a heat transfer section 52 which is heat transferring means extending from part of the outer circumference of the heat radiation section 51 backward in a predetermined width, a first heat absorbing section 53 which is one of heat absorbing means extending from one side of the heat transfer section 52, a second heat absorbing section 54 which is one of heat absorbing means extending from the other side of the heat transfer section 52, and a third heat absorbing section 55 which is one of the heat absorbing means extending from both sides of the heat transfer section 52 in that order from the distal end side. The respective heat absorbing sections 53 to 55 are provided with a plurality of creases along the longitudinal direction of the heat transfer member 50.

This heat transfer member 50 has a configuration similar to that of a so-called flexible printed circuit board (FPC) and has a structure with a metal foil (thin metal sheet) formed on an insulating film-shaped base film. The film-shaped insulator is made of a polyimide film or photo solder resist film, formed into a metal foil such as copper having excellent thermal conductivity in consideration of cost, printed (plated) on a film or the metal foil (thin metal sheet) is pasted to the film. The copper metal foil has a continuous metal pattern having a shape substantially matching the shapes of heat radiation section 51, the heat transfer section 52, the first heat absorbing section 53, the second heat absorbing section 54 and the third heat absorbing section 55 with the respective rims being positioned slightly inward from the rims of the respective sections 51 to 55.

To be more specific, the ring-shaped heat radiation section 51 is provided with a heat radiation metal section 61 which is a ring-shaped metal foil. This heat radiation metal section 61 is formed so as to be exposed on one surface side which is the front end face of the heat radiation section 51.

The heat transfer section 52 is provided with a heat transfer metal section 62 which continuously extends from part of the outer circumference of the heat radiation metal section 61. This heat transfer metal section 62 is formed so as to be covered with the film of the heat transfer section 52. The heat transfer metal section 62 may also be covered with a heat insulating film such as foaming film so as to improve heat insulating properties and prevent heat from transmitting to other components unnecessarily in addition to a polyimide film or photo solder resist film. The present embodiment describes one heat transfer section 52 here, but a plurality of heat transfer sections 52 may be provided.

The respective heat absorbing sections 53 to 55 are provided with first to third heat absorbing metal sections 63 to 65 that continuously extend from one side of the heat transfer metal section 62. The heat absorbing metal sections 63 to 65 are provided so as to be exposed from one surface side of the respective heat absorbing sections 53 to 55 to improve heat absorbing properties.

The heat transfer member 50 configured as shown above is arranged in the distal end portion 11.

To be more specific, the heat radiation section 51 of the heat transfer member 50 is adhered to the rear surface of the transparent cover member 22 (surface in the distal end portion 11) using, for example, a UV adhesive (see FIG. 2 to FIG. 4). In this case, the heat radiation section 51 is adhered so that the surface of the heat radiation metal section 61 contacts the rear surface of the transparent cover member 22.

The heat radiation section 51 has an outer circumference shape which is substantially the same as or slightly smaller than the outer circumference shape of the transparent cover member 22 and an aperture size that does not interfere with the image-pickup field of view of the image pickup unit 30 is set. Here, a configuration is adopted in which the heat radiation section 51 is adhered to the transparent cover member 22 using an adhesive or the like, but without being limited thereto, it is also possible to adopt a configuration in which the front end face of the second support frame 31 presses the heat radiation section 51 against the rear surface of the transparent cover member 22 so that the surface of the heat radiation metal section 61 contacts the surface of the transparent cover member 22.

Furthermore, as shown in FIG. 4 and FIG. 6, the distal end portion of the heat transfer section 52 of the heat transfer member 50 is inserted and arranged in a concave section 31a notched inward from the outer circumferential portion in the rib part disposed on the distal end side of the second support frame 31 that engages with the first lens holding frame 33. That is, the heat transfer section 52 is arranged between the support frames 20 and 31 at a position at which the first support frame 20 engages with the second support frame 31. Thus, the first support frame 20 and the second support frame 31 can prevent the size in the outside diameter direction of the distal end portion 11 from increasing due to the arrangement of the heat transfer section 52 and can also be coupled together by being sufficiently hermetically sealed through the engagement of the proximal end portions.

Furthermore, as shown in FIG. 4 and FIG. 7, some midpoint of the heat transfer section 52 is inserted and arranged in a concave section 35a of the second lens holding frame 35 notched inward from the outer circumferential portion. That is, regarding the engagement position of the second support frame 31 and the second lens holding frame 35, the heat transfer section 52 is arranged between the second support frame 31 and the second lens holding frame 35. Here, it is also possible to prevent the size in the outside diameter direction of the distal end portion 11 from increasing due to the arrangement of the heat transfer section 52, and since the proximal end outer circumference of the second lens holding frame 35 is covered with the thermal contraction tube 47, internal hermeticity is kept.

The rear side of the heat transfer section 52 is arranged along the outer circumference of the unit holding frame 36. Here, the perimeter of the unit holding frame 36 is an area not engaged with the distal end rigid portion 23 and does not influence the size of the outside diameter direction of the distal end portion 11 and moreover, hermeticity is sufficiently kept because the unit holding frame 36 is covered with the thermal contraction tube 47.

As shown in FIG. 4, at the position where the second image pickup device 45 is provided, the first heat absorbing section 53 of the heat transfer member 50 is arranged so as to cover the perimeter of the second image pickup device 45. Furthermore, at the position where the first image pickup device 42 is provided, the second heat absorbing section 54 is arranged so as to cover the perimeter of the first image pickup device 42. Furthermore, at the positions where the two image pickup processing circuits 43 and 46 are provided, the third heat absorbing section 55 is arranged so as to integrally cover the perimeters of the image pickup processing circuits 43 and 46.

The respective heat absorbing sections 53 to 55 are provided with the aforementioned creases so as to easily cover the perimeters of the image pickup devices 42 and 45 or the image pickup processing circuits 43 and 46. Furthermore, the respective heat absorbing sections 53 to 55 are arranged so that one surface from which their respective heat absorbing metal sections 63 to 65 are exposed is on the side of the respective image pickup devices 42 and 45 or the side of the respective image pickup processing circuits 43 and 46.

The perimeters of the respective image pickup devices 42 and 45, and the respective image pickup processing circuits 43 and 46 are covered with a filling member and covered with the respective heat absorbing sections 53 to 55 via the filling member, and therefore insulation between the exposed metal foil and the heat absorbing metal sections 63 to 65 is kept. Furthermore, after covering the perimeters of the respective image pickup devices 42 and 45 or the perimeters of the image pickup processing circuits 43 and 46, the respective heat absorbing sections 53 to 55 are covered with the thermal contraction tube 47.

As described above, the endoscope apparatus 1 of the present embodiment is provided so that the respective heat absorbing section 53 to 55 of the heat transfer member 50 disposed in the distal end portion 11 cover the perimeters of the respective image pickup devices 42 and 45 and respective image pickup processing circuits 43 and 46 which generate heat when the image pickup unit 30 is driven.

Therefore, as shown in FIG. 8, heat H of the respective image pickup devices 42 and 45 and the respective image pickup processing circuits 43 and 46 which become heating elements (heat sources) of the present embodiment is absorbed (heat transferred) by the heat absorbing metal section 63 to 65 of the respective heat absorbing sections 53 to 55. The heat H transferred to the heat absorbing metal sections 63 to 65 is transmitted to the heat transfer metal section 62 of the heat transfer section 52 and transferred to the heat radiation metal section 61 of the heat radiation section 51 on the distal end side. The heat H transferred to the heat radiation section 51 is radiated (thermal radiation) to the transparent cover member 22 that surface-contacts the heat radiation metal section 61. That is, heat H of the heat radiation metal section 61 of the heat radiation section 51 arranged in the vicinity of the rear surface outer circumference edges is transmitted to the transparent cover member 22, which is heated inward from the outer circumferential portion, that is, toward the center at which the optical axis O passes.

Thus, the endoscope apparatus 1 is configured so that heat of the respective image pickup devices 42 and 45 and the respective image pickup processing circuits 43 and 46 of the image pickup unit 30 is transferred to the transparent cover member 22 via the heat transfer member 50 so as to heat the transparent cover member 22.

Here, a medical rigid endoscope such as the endoscope apparatus 1 of the present embodiment especially used for laparoscopic surgical operation is inserted from an ambient temperature of about 20° C. in an operation room into the abdominal cavity at an ambient temperature about 41° C. and humidity 100%. Due to the temperature difference between the outside air and the abdominal cavity and humidity, fogging occurs due to condensation on the outer surface of the transparent cover member 22 which is an observation window provided at the distal end portion 11 of the endoscope apparatus 1.

However, the endoscope apparatus 1 of the present embodiment provides the heat transfer member 50 in the distal end portion 11 to absorb heat H generated in the respective sections utilizing heat generation at the respective image pickup devices 42 and 45 and the respective image pickup processing circuits 43 and 46, transfer heat to a remote position and cause the heat H transmitted to the transparent cover member 22 to radiate. Thus, the endoscope apparatus 1 heats the transparent cover member 22 which is an observation window disposed so as to be exposed from the front (distal end face) of the distal end portion 11, and can thereby prevent fogging, condensation or the like from occurring on the outer surface of the transparent cover member 22.

This eliminates the necessity for the user, who is a medical doctor, to pull out the insertion portion 2 of the endoscope apparatus 1 from within the abdominal cavity once to wipe the outer surface of the transparent cover member 22. Therefore, the endoscope apparatus 1 of the present embodiment can prevent operation by the medical doctor from becoming complicated without increasing the manipulation time.

Furthermore, in the endoscope apparatus 1 of the present embodiment, since the two image pickup devices 42 and 45 and the two image pickup processing circuits 43 and 46 are arranged within a narrow space of the distal end portion 11 to realize high-pixel, high quality color reproduction, heat generation from the respective image pickup devices 42 and 45 and the respective image pickup processing circuits 43 and 46 in particular causes the ambient temperature to increase, causing noise which is harmful to electronic parts. However, as described above, the endoscope apparatus 1 of the present embodiment can suppress temperature rises of the respective image pickup devices 42 and 45 and the respective image pickup processing circuits 43 and 46 using the heat transfer member 50, and can thereby also suppress the occurrence of electric noise which is harmful to picked-up images and which increases as the temperature of the electronic part increases.

Furthermore, the endoscope apparatus 1 of the present embodiment has a configuration in which the perimeters of the respective image pickup devices 42 and 45 and the respective image pickup processing circuits 43 and 46 are covered with the heat absorbing metal sections 63 to 65 of the respective heat absorbing sections 53 to 55 of the heat transfer member 50. Thus, the endoscope apparatus 1 of the present embodiment can also be configured to be effective as a measure for electromagnetic compatibility (EMC). That is, the respective image pickup devices 42 and 45 and the respective image pickup processing circuits 43 and 46 are prevented from producing electromagnetic interference which would affect the outside, and can also be driven within a tolerable range of electromagnetic sensitivity to influences from outside electromagnetic waves or the like.

Particularly, with the technical advance of electronic parts such as semiconductor chips provided on the respective image pickup devices 42 and 45 and the respective image pickup processing circuits 43 and 46, those electronic parts are designed to be able to be driven with small power and in a small and fine configuration, but their electromagnetic resistance is inevitably reduced correspondingly. However, since the respective heat absorbing metal sections 63 to 65 which are metal foils serve as an electromagnetic shield, covering various electronic parts provided in the respective image pickup devices 42 and 45 and the respective image pickup processing circuits 43 and 46, the endoscope apparatus 1 of the present embodiment has an advantage of making the electronic parts less likely to be adversely affected by outside electromagnetic waves.

The heat transfer member 50 that transfers heat of the respective image pickup devices 42 and 45 and the respective image pickup processing circuits 43 and 46 to the transparent cover member 22 which is an observation window is not limited to the aforementioned configuration, but the heat transfer section 52 may be changed to a configuration of heat pipe, electric heating cable or the like.

Furthermore, although the endoscope apparatus 1 of the present embodiment has been described taking a rigid endoscope for surgical therapy as an example, the endoscope apparatus 1 of the present embodiment is a technique applicable to various types of medical or industrial endoscope apparatuses.

(Second Embodiment)

Next, a second embodiment of the present invention will be described.

Figure 9:
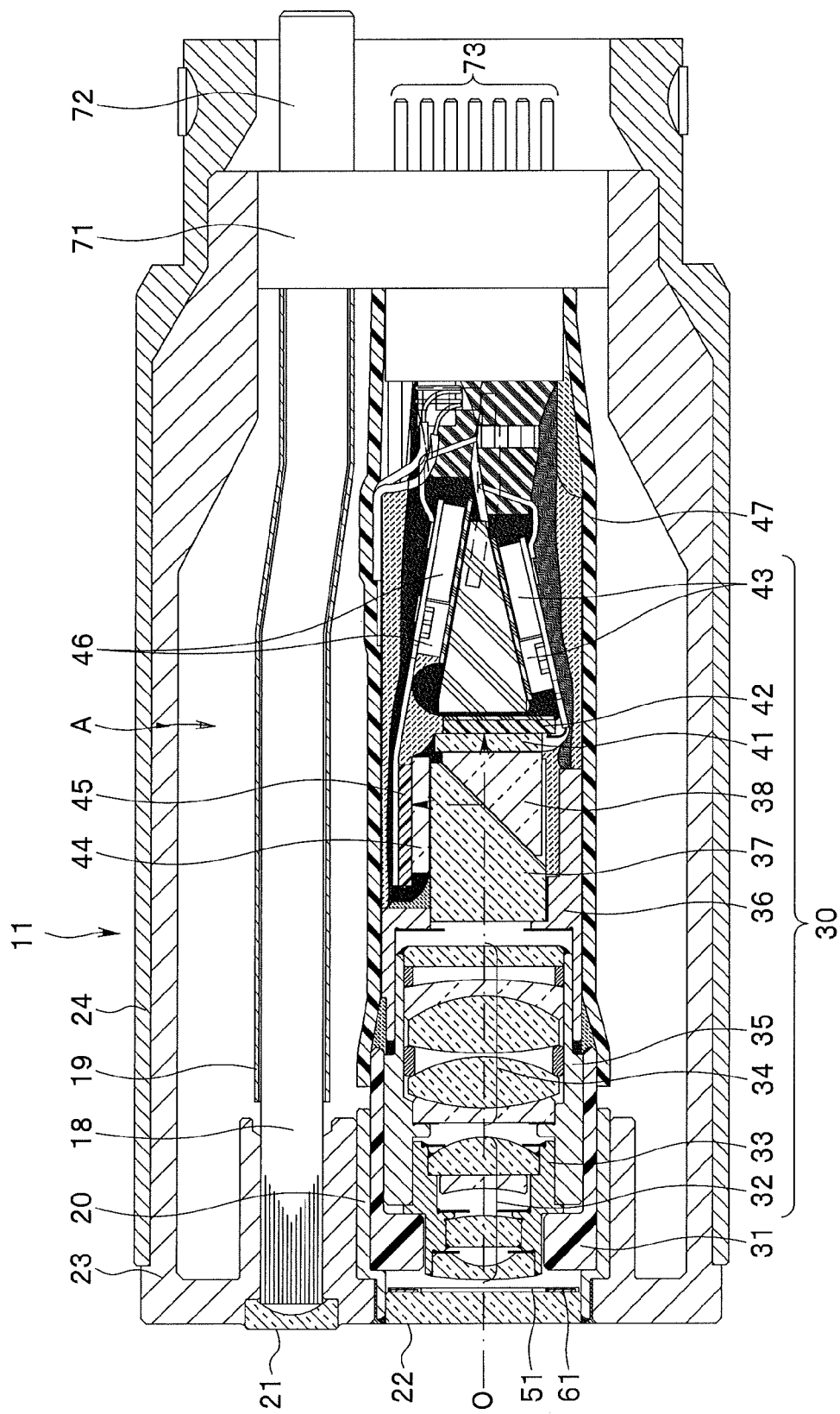
FIG. 9 is a cross-sectional view of a distal end portion of an insertion portion according to a second embodiment of the present invention.

FIG. 9 is related to the second embodiment of the present invention and FIG. 9 is a cross-sectional view of a distal end portion of an insertion portion. In the present embodiment, the components described in the first embodiment will be assigned the same reference numerals and detailed explanations thereof will be omitted.

The present embodiment will illustrate the endoscope apparatus 1 in which the interior of the distal end portion 11 incorporating the heat transfer member 50 for preventing fogging due to condensation of the transparent cover member 22 which is an observation window as in the case of the first embodiment is in quasi-vacuum (ultra-high vacuum) or perfect vacuum.

As shown in FIG. 9, in the distal end portion 11, a space A of the distal end rigid portion 23 is in ultra-high vacuum or perfect vacuum. In other words, the space A surrounding the internal components such as the image pickup unit 30 and the light guide bundle 18 arranged in the distal end rigid portion 23 is in ultra-high vacuum or perfect vacuum.

To keep the inside in ultra-high vacuum or perfect vacuum and mechanically or electrically connect the inner components such as the image pickup unit 30 and the light guide bundle 18 to the rear side, that is, the bending portion 12 side, the proximal end portion of the distal end rigid portion 23 is hermetically sealed by a hermetic connector 71.

In the hermetic connector 71, the inside of its metallic sheath is sealed with glass and kept perfectly airtight and a light guide connector terminal 72 for mechanically connecting the light transmission path of the light guide bundle 18 and an electric connection terminal 73 for electrically connecting the image pickup unit 30 or the like are disposed on the proximal end face.

As described above, since the inside of the distal end portion 11 is in ultra-high vacuum or perfect vacuum, the endoscope apparatus 1 of the present embodiment has a heat insulating structure in which heat generated in the image pickup unit 30 is less likely to transmit in the outer circumference direction of the distal end portion 11 and has a configuration in which the perimeter of the image pickup unit 30 is substantially thermally insulated.

In the endoscope apparatus 1 configured as shown above, heat H generated in the respective image pickup devices 42 and 45 and the respective image pickup processing circuits 43 and 46 disposed in the image pickup unit 30 in the distal end portion 11, which become heating elements (heat sources), is transmitted to the distal end side of the image pickup unit 30 mainly via the heat transfer member 50 due to heat insulating properties of the atmosphere space (space A of the distal end rigid portion 23) in the circumferential direction of the image pickup unit 30. The heat H generated above is, of course, transferred to the respective holding frames 33, 35 and 36 and the respective support frames 20 and 21.

That is, the endoscope apparatus 1 has a structure in which the heat H generated in the respective image pickup devices 42 and 45 and the respective image pickup processing circuits 43 and 46 of the image pickup unit 30 is efficiently absorbed from the heat absorbing metal sections 63 to 65 of the respective heat absorbing sections 53 to 55 of the heat transfer member 50. The heat H transferred to the heat absorbing metal sections 63 to 65 is transmitted to the heat transfer metal section 62 of the heat transfer section 52 in the same way as in the first embodiment described using FIG. 8 and transferred to the heat radiation metal section 61 of the heat radiation section 51 on the distal end side.

The heat H transferred to the heat radiation section 51 is radiated (thermal radiation) to the transparent cover member 22 that surface-contacts the heat radiation metal section 61 in the same way as in the first embodiment and the transparent cover member 22 is heated. Thus, the endoscope apparatus 1 of the present embodiment can prevent the occurrence of fogging, condensation or the like on the outer surface of the transparent cover member 22 in the same way as in the first embodiment.

In addition to the operation and effect, for various connections of the image pickup unit 30 which is an electronic device incorporated in the distal end portion 11 and the light guide bundle 18 which is an illuminating light transmission part, the endoscope apparatus 1 of the present embodiment for medical use uses the hermetic connector 71 for hermetically sealing the distal end rigid portion 23, and thereby improves the resistance of autoclave (high-temperature, high-pressure sterilization processing).

Furthermore, the inner components such as the image pickup unit 30, the light guide bundle 18 or the like of the distal end portion 11 are in a unit configuration integrated by the hermetic connector 71. Therefore, in the endoscope apparatus 1 of the present embodiment the hermetic connector 71 is removed from the distal end rigid portion 23, and thereby also has an advantage of improving various types of maintainability such as exchange of the inner components and repair of malfunction of the unitized distal end portion 11 and being able to reduce maintenance cost.

The present invention described above is not limited to the above described embodiments, but various modifications can be made without departing from the spirit and scope of the invention at implementation stages. Furthermore, the respective embodiments include inventions at various stages and various kinds of invention may be extracted by an appropriate combination of a plurality of configuration requirements disclosed.

For example, even when several configuration requirements are deleted from all configuration requirements shown in the embodiments, if the referred effects are obtained for problems to be solved by the invention, the configurations from which such configuration requirements have been deleted may be extracted as the invention.

What is claimed is:

1. An endoscope apparatus comprising:
    an insertion portion inserted into a body;
    an optical member as an observation window arranged exposed from an outside surface at a distal end of the insertion portion;
    an objective optical system that condenses light impinged from the optical member;
    an electronic image pickup circuit that photoelectrically converts photographing light condensed by the objective optical system;
    a flexible film member disposed in the insertion portion and formed by an insulating, flexible member;
    a heat absorbing section disposed at one end part of the flexible film and having a first metal pattern formed thereon, the first metal pattern being arranged opposed to the electronic image pickup circuit so as to encircle the electronic image pickup circuit and absorbing heat generated from the electronic image pickup circuit;
    a heat radiation section disposed at the other end part of the flexible film member and having a second metal pattern formed thereon, the second metal pattern being adhered to the optical member in surface contact therewith at a position where the second metal pattern does not interfere with the photographing light to be condensed by the objective optical system and impinged on the electronic image pickup circuit on a rear surface of the optical member which is opposite to an exposed surface of the optical member, and the second metal pattern radiating heat transferred from the heat absorbing section to the optical member and adapted to prevent fogging, condensation or the like from occurring on the exposed surface of the optical member; and
    a heat transfer section provided to connect the heat absorbing section and the heat radiation section between the one end part and the other end part of the flexible film member and having a third metal pattern formed thereon, the third metal pattern connecting the first metal pattern of the heat absorbing section and the second metal pattern of the heat radiation section to be capable of heat transfer.

2. The endoscope apparatus according to claim 1, further comprising:
    a first support frame that holds the optical member;
    a second support frame, part of a distal end of which engages with the first support frame, for holding an image pickup unit comprising the objective optical system, the electronic image pickup circuit or the like; and
    an optical system holding frame that engages with a part closer to a proximal end portion than the part of the distal end of the second support frame and holds the objective optical system,
    wherein the flexible film is arranged between the first support frame and the second support frame and between the second support frame and the optical system holding frame.

3. The endoscope apparatus according to claim 2, wherein a concave section in which the flexible film can be inserted and arranged is formed in the second support frame and the optical system holding frame.

4. The endoscope apparatus according to claim 1, wherein the heat radiation section is formed in a ring-shape with an opening that does not interfere with the photographing light, and adhered to an edge of the optical member in surface contact therewith.

5. The endoscope apparatus according to claim 1, wherein
    the electronic image pickup circuit comprises a plurality of solid image pickup devices that perform photoelectrical conversion of the photographing light impinged and a plurality of image pickup processing circuits that process photographing signals photoelectrically converted by the plurality of solid image pickup devices; and
    a plurality of heat absorbing sections that absorb the heat generated by the plurality of solid image pickup devices and the plurality of image pickup processing circuits by individually encircling the plurality of solid image pickup devices and integrally encircling the plurality of image pickup processing circuits.

6. The endoscope apparatus according to claim 1, wherein the second metal pattern is exposed on at least one surface side thereof to radiate heat transferred from the first metal pattern to the optical member.

7. The endoscope apparatus according to claim 1, wherein the first metal pattern is exposed on at least one surface side thereof to absorb heat generated from the electronic image pickup circuit.

8. The endoscope apparatus according to claim 7, wherein the second metal pattern is exposed on at least one surface side thereof to radiate heat transferred from the first metal pattern to the optical member.

* * * * *